(12) United States Patent
Mitchell

(10) Patent No.: US 8,617,079 B2
(45) Date of Patent: Dec. 31, 2013

(54) ECHOGENIC MEDICAL NEEDLE

(75) Inventor: Christopher Mitchell, Swanbourne (AU)

(73) Assignee: Coco Research Pty Ltd., Swanbourne (AU)

( * ) Notice: Subject to any disclaimer, the term of this patent is extended or adjusted under 35 U.S.C. 154(b) by 30 days.

(21) Appl. No.: 13/056,402

(22) PCT Filed: Jul. 24, 2009

(86) PCT No.: PCT/AU2009/000944
§ 371 (c)(1),
(2), (4) Date: Mar. 10, 2011

(87) PCT Pub. No.: WO2010/012023
PCT Pub. Date: Feb. 4, 2010

(65) Prior Publication Data
US 2011/0160592 A1    Jun. 30, 2011

(30) Foreign Application Priority Data
Jul. 29, 2008 (AU) .................................. 2008903866

(51) Int. Cl.
*A61B 8/00* (2006.01)
(52) U.S. Cl.
USPC ........................................ 600/461; 600/437
(58) Field of Classification Search
USPC ................................................ 600/437–469
See application file for complete search history.

(56) References Cited

U.S. PATENT DOCUMENTS

| | | | |
|---|---|---|---|
| 4,207,901 A | 6/1980 | Nigram | |
| 4,249,539 A | 2/1981 | Vilkomerson | |
| 4,401,124 A | 8/1983 | Guess et al. | |
| 4,431,006 A | 2/1984 | Trimmer et al. | |
| 4,642,168 A | 2/1987 | Imai | |
| 5,490,521 A | 2/1996 | Davis et al. | |
| 5,759,154 A | 6/1998 | Hoyns | |
| 5,766,135 A | 6/1998 | Terwilliger | |
| 6,053,870 A | 4/2000 | Fulton, III | |
| 6,358,211 B1 | 3/2002 | Mamayek | |
| 6,723,052 B2 | 4/2004 | Mills | |
| 2003/0135117 A1 | 7/2003 | Ward et al. | |
| 2004/0249288 A1 | 12/2004 | Ichikawa | |
| 2005/0215849 A1 | 9/2005 | Choay et al. | |

(Continued)

FOREIGN PATENT DOCUMENTS

FR           2272633         12/1975
JP     2004 181095 A        7/2004

OTHER PUBLICATIONS

International Preliminary Report on Patentability (PCT/AU2009/000944) issued Feb. 1, 2011.

(Continued)

*Primary Examiner* — Sanjay Cattungal
(74) *Attorney, Agent, or Firm* — Clark & Elbing LLP; Karen L. Elbing

(57) ABSTRACT

There is disclosed a medical needle comprising a needle shaft that defines a longitudinal axis, a tip formed at one end of the shaft, and an ultrasonic reflector formed in an outer surface of the needle shaft. The reflector comprises a first reflector surface that is at an angle of no more than 35° to the longitudinal axis of the shaft and that faces towards the tip, and at least one additional reflector surface that forms an angle to the first reflector surface within the range of 75° to 105°, and that is substantially concave in a direction towards the first reflector surface.

15 Claims, 17 Drawing Sheets

(56) References Cited

U.S. PATENT DOCUMENTS

| | | |
|---|---|---|
| 2005/0228288 A1 | 10/2005 | Hurst |
| 2006/0241489 A1 | 10/2006 | Hiki et al. |
| 2007/0167822 A1 | 7/2007 | Webler et al. |
| 2007/0265516 A1 | 11/2007 | Wang |
| 2008/0058702 A1 | 3/2008 | Arndt et al. |
| 2008/0097213 A1 | 4/2008 | Carlson et al. |
| 2009/0137906 A1 | 5/2009 | Maruyama et al. |

OTHER PUBLICATIONS

International Search Report (PCT/AU2009/000944) mailed Sep. 7, 2009.

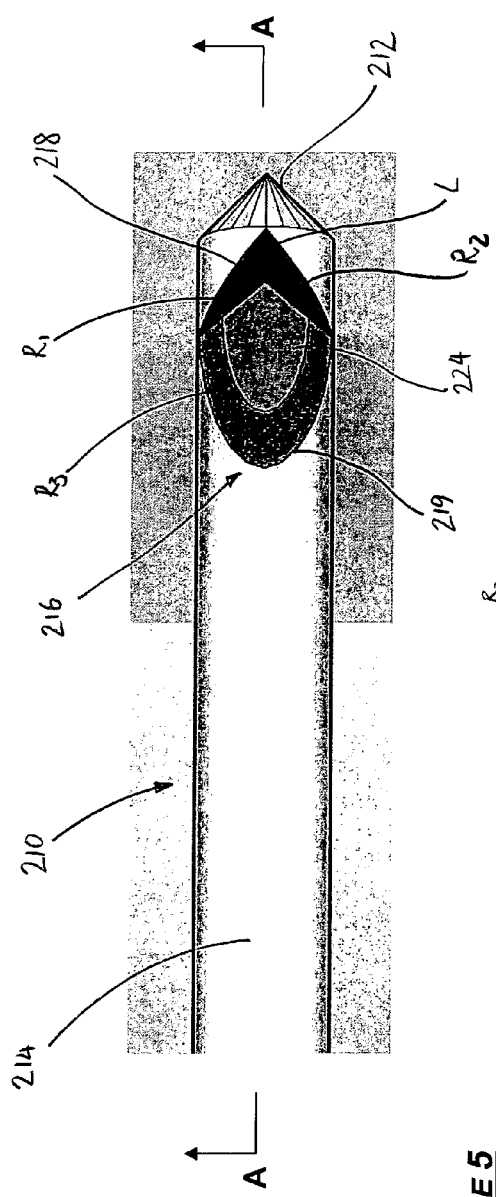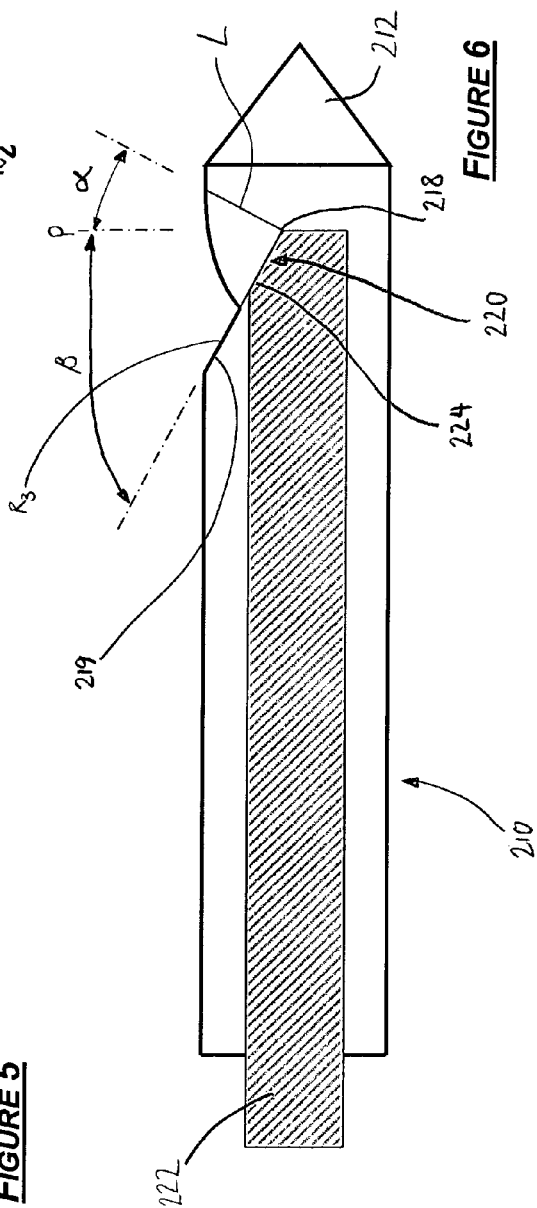
FIGURE 5
FIGURE 6

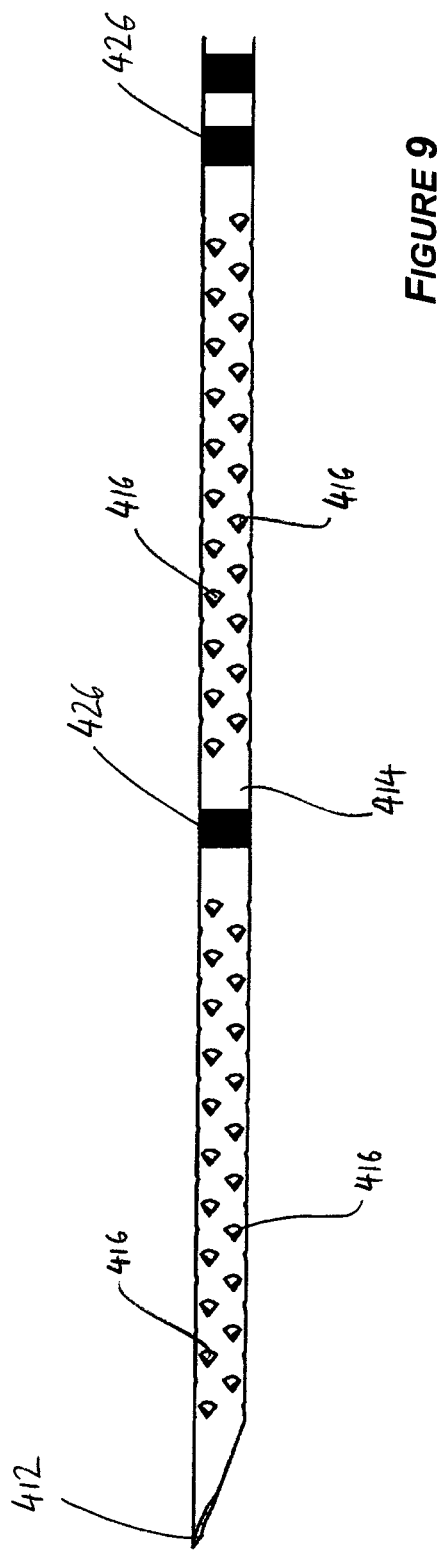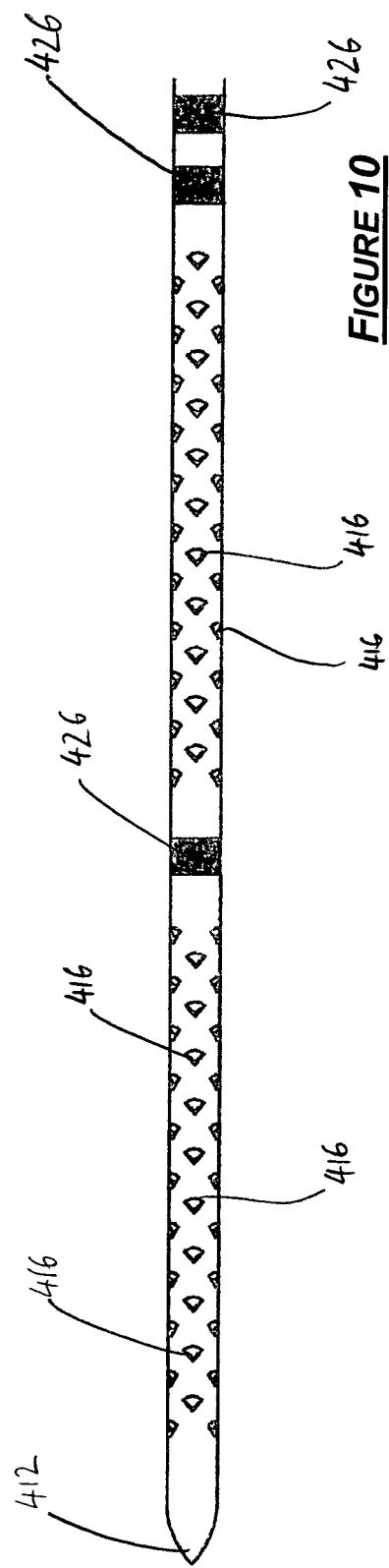

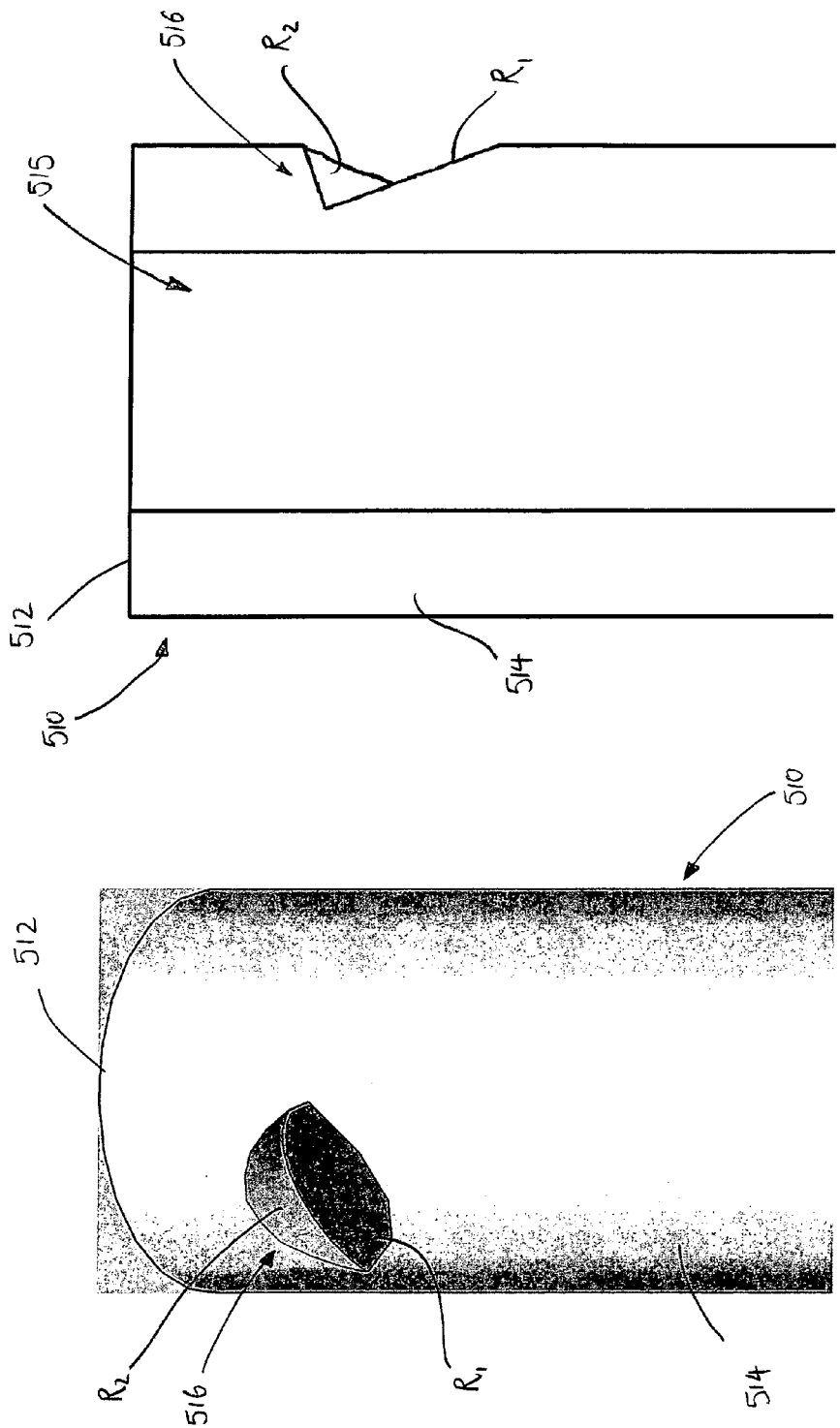

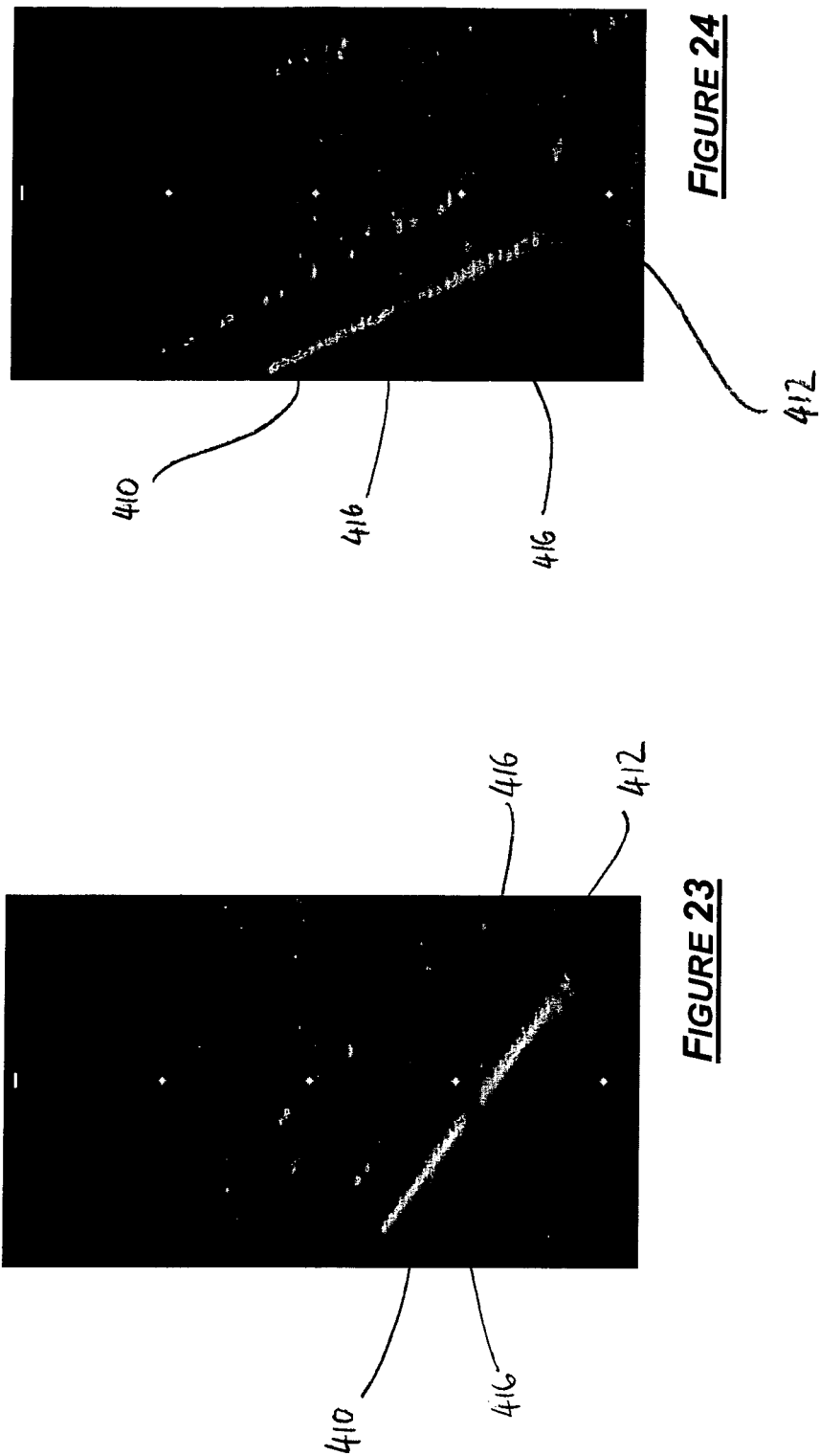

ECHOGENIC MEDICAL NEEDLE

CROSS REFERENCE TO RELATED APPLICATIONS

This application is the U.S. National Stage of International Application No. PCT/AU2009/000944, filed Jul. 24, 2009, which claims the benefit of Australian Patent Application No. 2008903866, filed Jul. 29, 2008, which is hereby incorporated by reference.

FIELD OF THE INVENTION

The present invention relates to a medical needle.

BACKGROUND

Medical needles are used in clinical procedures to pierce tissue in order to deliver fluids containing pharmaceutical compounds subcutaneously, and also to gather tissues, cells and/or bodily fluid for diagnostics. In certain procedures, it is desirable to insert the needle tip to a specific location. For example, in some anaesthetic procedures, anaesthetic may need to be delivered beside a nerve.

Misplacement of the needle and needle related injury are a significant concern to the proceduralist and patient. In certain procedures it is particularly important to avoid piercing or damaging nerves, veins, arteries, and other organs/entities during insertion of the needle. For these reasons, proceduralists use many techniques for identifying the location of the needle tip.

It is now relatively common to use ultrasound to confirm needle positioning during procedures. This involves the use of ultrasound waves to observe, in real time, the position of the needle tip. Ultrasound waves are introduced by a transducer. The ultrasound waves received by the transducer are used generate an image.

The ultrasound waves are readily reflected by changes in material density. In this context, changes between layers of tissue, tissue and nerve fibres, and medical equipment (including needles) and tissue are all capable of reflecting ultrasound waves. An ultrasound wave is strongly reflected at the interface of the two materials, such as a needle/tissue interface.

Where the needle/tissue interface is perpendicular to ultrasound waves emitted from a transducer, the waves can be reflected directly back to the transducer. This produces a very clear ultrasound image of the needle within the tissue. However, in most cases the needle is at an oblique angle to the transducer, so the needle/tissue interface is oblique to the emitted ultrasound wave. This results in the ultrasound waves being reflected away from the transducer, which decreases the visibility of the needle in the ultrasound image. This problem is exacerbated with steep angles of insertion; that is, as the needle approaches the parallel to the emitted ultrasound waves.

In some cases, the needle can only be seen in the ultrasound image as a silhouette in the surrounding tissue. In other words, the needle location can be determined in the ultrasound image by an echogenic shadow created by the needle.

It is known to provide medical needles for insertion into a patient that have an ultrasonic reflector formed in the outer surface for reflecting ultrasound waves back towards the source. It is also known to provide a number of such reflectors dispersed over the surface of a medical needle.

The present invention seeks to provide a medical needle with increased visibility in ultrasound guided procedures.

SUMMARY OF THE INVENTION

The present invention provides a medical needle comprising a needle shaft that defines a longitudinal axis, a tip formed at one end of the shaft, and an ultrasonic reflector formed in an outer surface of the needle shaft, the reflector comprising:

a first reflector surface that is at an angle of no more than 35° to the longitudinal axis of the shaft and that faces towards the tip, and at least one additional reflector surface that forms an angle to the first reflector surface within the range of 75° to 105°, and that is substantially concave in a direction towards the first reflector surface.

The present invention also provides a medical needle comprising a needle shaft defining a longitudinal axis, a tip formed at one end of the shaft, and an ultrasonic reflector formed in an outer surface of the needle shaft, the reflector comprising:

a first reflector surface that is at an angle of no more than 35° to the longitudinal axis of the shaft and facing towards the tip, and at least one additional reflector surface that forms an angle to the first reflector surface within the range of 75° to 105°, and that has two or more convergent normals.

In some embodiments, the reflector is symmetrical about a plane that includes the longitudinal axis of the needle shaft.

In certain embodiments, the first reflector surface is at an angle of approximately 20° to the longitudinal axis.

The first reflector surface may be planar.

In some embodiments, the at least one additional reflector surface comprises at least two reflector surfaces that intersect with each other. The at least two additional reflector surfaces may be planar.

In particular embodiments, the at least one additional reflector surface consists of two additional reflector surfaces, and wherein the first reflector surface and the two additional reflector surfaces are disposed at an angle to one another within the range of 75° to 105°.

The first reflector surface and the two additional reflector surfaces may be mutually orthogonal to one another.

In some embodiments, the at least one additional reflector surface comprises a single additional reflector surface that includes a curved portion. The curved portion can form a circular arc. Furthermore, the circular arc may subtend an angle in the range of 60° to 180°.

The present invention also provides a medical needle comprising:

a tip formed at one end of a needle shaft, and an ultrasonic reflector formed in the outer surface of the needle shaft and having three reflector surfaces that intersect to form a reflector vertex, the reflector being orientated with a first line of intersection between two intersecting reflector surfaces extending from the reflector vertex towards the needle tip, and forming an angle of less than 35° with respect to a line extending radially outwardly of the needle body from the reflector vertex.

The angle of the first line of intersection with respect to the line extending radially outwardly from the reflector vertex can be within the range of 10° to 35°.

The angle of the first line of intersection with respect to the line extending radially outwardly from the reflector vertex can be approximately 25°.

The angle of the first line of intersection with respect to the line extending radially outwardly from the reflector vertex can be approximately 30°.

The present invention also provides a medical needle comprising:

a tip formed at one end of a needle shaft, the shaft defining a longitudinal axis, and an ultrasonic reflector formed in an outer surface of the needle shaft and having three reflector surfaces that intersect to form a reflector vertex, the reflector being orientated with a first of the three reflector surfaces located entirely rearwardly of the reflector vertex with respect to the needle tip and being at an angle of no more than 35° to the longitudinal axis and facing towards the tip, and the reflector being symmetrical about a plane that is co-incident with the longitudinal axis of the needle shaft.

The first reflector surface can be at an angle to the longitudinal axis within the range of 10° to 35°.

In some embodiments, the first reflector surface is at an angle of 25° to the longitudinal axis. In some other embodiments, the first reflector surface is at an angle of 20° to the longitudinal axis.

Each of the three reflector surfaces may be planar.

The three reflector surfaces may be mutually orthogonal.

The reflector can be one of a plurality of like reflectors formed the outer surface of the needle shaft.

In certain embodiments, the plurality of reflectors are arranged in one or more series of reflectors, each series extending along linearly the needle shaft.

The or each series can be constructed of a repeating pattern.

In certain embodiments, the or each series extends longitudinally along the needle shaft.

In certain embodiments, the or each series consists of two or more sets of reflectors, the sets being spaced longitudinally along the shaft of the needle.

The medical needle may further comprise graduations marked on the outer surface of the needle, wherein one of the graduations is disposed between adjacent sets of reflectors in the or each series.

In at least one embodiment, the plurality of reflectors are arranged in six series of reflectors that are spaced circumferentially around the outer surface of the needle. Each series may be offset longitudinally with respect to the adjacent series.

In certain embodiments, the needle further comprises:

a lumen that extends from the rear end of the needle towards the needle tip; and a lateral port that opens into the reflector and is in communication with the lumen.

The lateral port may be formed rearwardly of the reflector vertex in one of the three reflector surfaces.

In certain embodiments, the needle further comprises a removable stylet that can be located in the lumen to close off the lateral port.

The stylet can further comprises an oblique ultrasonic reflective planar surface that forms part of the reflector of the needle.

The oblique planar surface of the stylet and a wall surface of the needle shaft can be aligned to form a mutually planar reflecting surface.

The present invention also provides a medical needle comprising a needle shaft that defines a longitudinal axis, a tip formed at one end of the shaft, and an ultrasonic reflector formed in an outer surface of the needle shaft, the reflector comprising:

a first reflector surface that is at an angle of no more than 35° to the longitudinal axis of the shaft and that faces towards the tip, and a second reflector surface that forms an angle to the first reflector surface within the range of 75° to 105°, and that is curved with concavity in a direction towards the first reflector surface.

The present invention also provides a method of performing an invasive medical procedure comprising:

providing a medical needle according to the present invention;

providing an ultrasonic transducer;

placing the transducer on a patient's outer skin and energizing the transducer to emit ultrasound waves into the patient;

inserting the needle into the patient adjacent the transducer such the ultrasound waves impinge on a portion of the needle that includes the ultrasonic reflector; and capturing a reflected ultrasonic wave from the ultrasonic reflector.

The step of inserting the needle into the patient may involve inserting the needle with the longitudinal axis of the needle lying in a plane that includes the emitted ultrasound waves.

The method may further comprise establishing angle of insertion of the needle such that the longitudinal axis of the needle and the emitted ultrasound waves form an angle that is at least equal to the angle of the first reflector surface relative to the longitudinal axis of the needle.

BRIEF DESCRIPTION OF THE DRAWINGS

In order that the invention may be more easily understood, embodiments are described, by way of example only, with reference to the accompanying drawings, in which:

FIG. 5: is a side elevation view of the needle of FIG. 4;

FIG. 6: is a cross section view of the needle of FIG. 5, as viewed along the line A-A;

FIG. 9: is a side elevation of region Y of the needle of FIG. 8;

FIG. 10: is a top view of region Y of the needle of FIG. 8;

FIG. 17: is a rear perspective view of the needle of FIG. 16;

FIG. 18: is a cross sectional view of the needle of FIG. 16, as viewed along the line D-D;

FIG. 23: is an ultrasound image of the needle of FIG. 8 embedded in gelatin; and FIG. 24: is a further ultrasound image of the needle of FIG. 8 embedded in gelatin.

DETAILED DESCRIPTION

Figure 1:
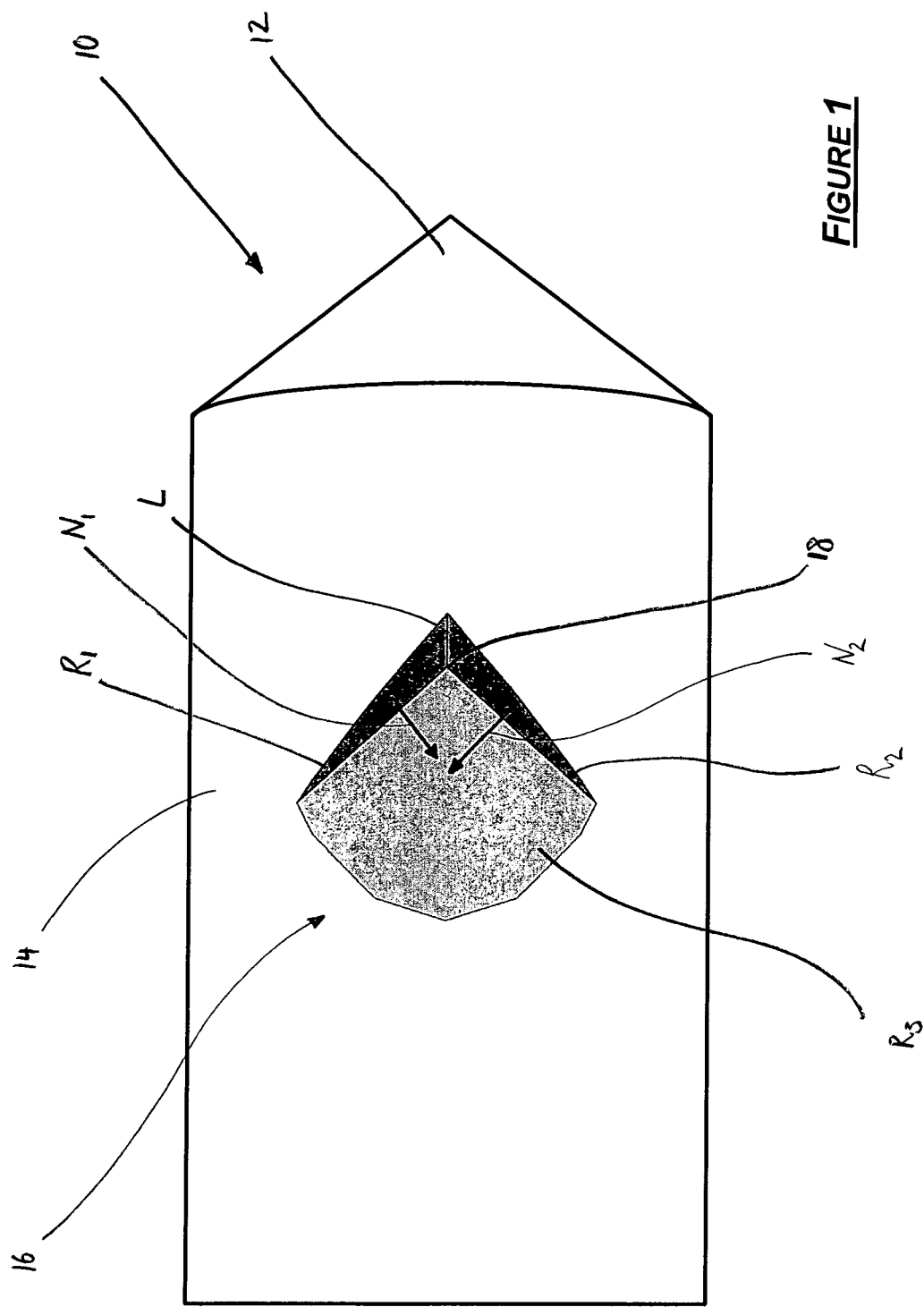
FIG. 1: is a side elevation view of a medical needle according to a first embodiment of the present invention.

FIG. 1 shows a medical needle 10 according to a first embodiment of the present invention. The needle 10 has a needle tip 12 at one end of the shaft 14. In this embodiment, the needle 10 defines a lumen (not shown) for delivering fluid, and/or extracting tissue, fluid or cells during a procedure. The needle shaft 14 defines a longitudinal axis.

The needle 10 has an ultrasonic reflector 16 formed in the outer surface of the needle shaft 14. In this embodiment, the reflector 16 is formed by three reflector surfaces. Each reflector surface intersects the other two reflector surfaces to form a reflector vertex. The angle between adjacent reflector surfaces is in the range of 75° to 105°. The reflector is orientated with the line L of intersection between two of the reflector surfaces extending from the vertex of the reflector towards the needle tip 12.

In this embodiment, the reflector 16 is in the form of a corner reflector, which has three mutually orthogonal, planar surfaces $R_1$, $R_2$, $R_3$. As described above, the corner reflector 16 is orientated with the line of intersection L between the two reflector surfaces $R_1$, $R_2$ extending in an inclined manner from the vertex 18 of the corner reflector towards the needle tip 12. In this way, the third surface $R_3$ is inclined rearwardly from the vertex 18 away from the needle tip 12, such that the third surface $R_3$ faces towards the needle tip 12. Furthermore, reflector surfaces $R_1$, $R_2$ are concave in the direction of the third reflector surface $R_3$. Lines $N_1$, $N_2$ that are normal to the respective reflector surfaces $R_1$, $R_2$ are convergent.

The line of intersection L between two surfaces $R_1$, $R_2$ forms an angle of less than 35° with a line extending radially outwardly of the needle 10 from the corner reflector vertex 18, which, in FIG. 1, would extend directly out of the page. In this embodiment, this angle is of the order of 25°. Accordingly, the third surface $R_3$ is inclined at an angle of 25° to the longitudinal axis of the needle 10, and faces towards the tip 12.

Furthermore, it can be seen from FIG. 1 that the third surface $R_3$ is located entirely rearwardly of the reflector vertex 18 with respect to the needle tip 12. In addition, the corner reflector 16 is symmetrical about a plane that is co-incident with the longitudinal axis of the needle shaft 14. As previously noted, in this embodiment the third surface $R_3$ is at an angle of approximately 25° to the longitudinal axis.

During a procedure in which the needle 10 is used, ultrasound waves can be emitted from a transducer (not shown). The surfaces of the corner reflector 16 reflect incident ultrasound waves back towards the transducer. Using the reflected ultrasound waves, an ultrasound image can be formed. The corner reflector 16 can show up on the ultrasound image as a prominent white spot, providing a visual marker of the position of that corner reflector 16 within surrounding tissue.

In procedures, it is very common for the transducer to be held perpendicular to the patient's skin immediately adjacent the needle puncture site. The needle is often held as close to perpendicular as possible. With the use of an ultrasound transducer and image to locate the needle, the relative angles between the needle shaft 14 and the ultrasound transducer are often at very acute angles. Orientating the corner reflector 16 on the shaft 14 of the needle 10, as described above, enables the corner reflector vertex 18 to be visible at acute angles between the shaft 14 and ultrasound transducer (in other words, at steep angles of insertion). Consequently, during procedures the corner reflector 16 more readily reflects ultrasound waves to the transducer, which increases visibility of the needle 10 at small angles. Furthermore, the above described orientation of the reflector 16 on the shaft 14 is able to accommodate a broad range of relative rotations of the needle 10 with respect to the plane of ultrasound waves whilst maintaining acceptable echogenicity of the reflector 16. This will be described in further detail in connection with FIG. 22.

In use of the needle 10, the proceduralist can see, in real time on the ultrasound image, the position of the corner reflector 16 within the surrounding tissue. This provides a very clear indication of the position of the needle tip 12 so that the tip can be positioned with increased precision. For example, the tip 12 can be quickly and accurately positioned, for example between two layers of tissue, adjacent a nerve, etc.

Figure 2:
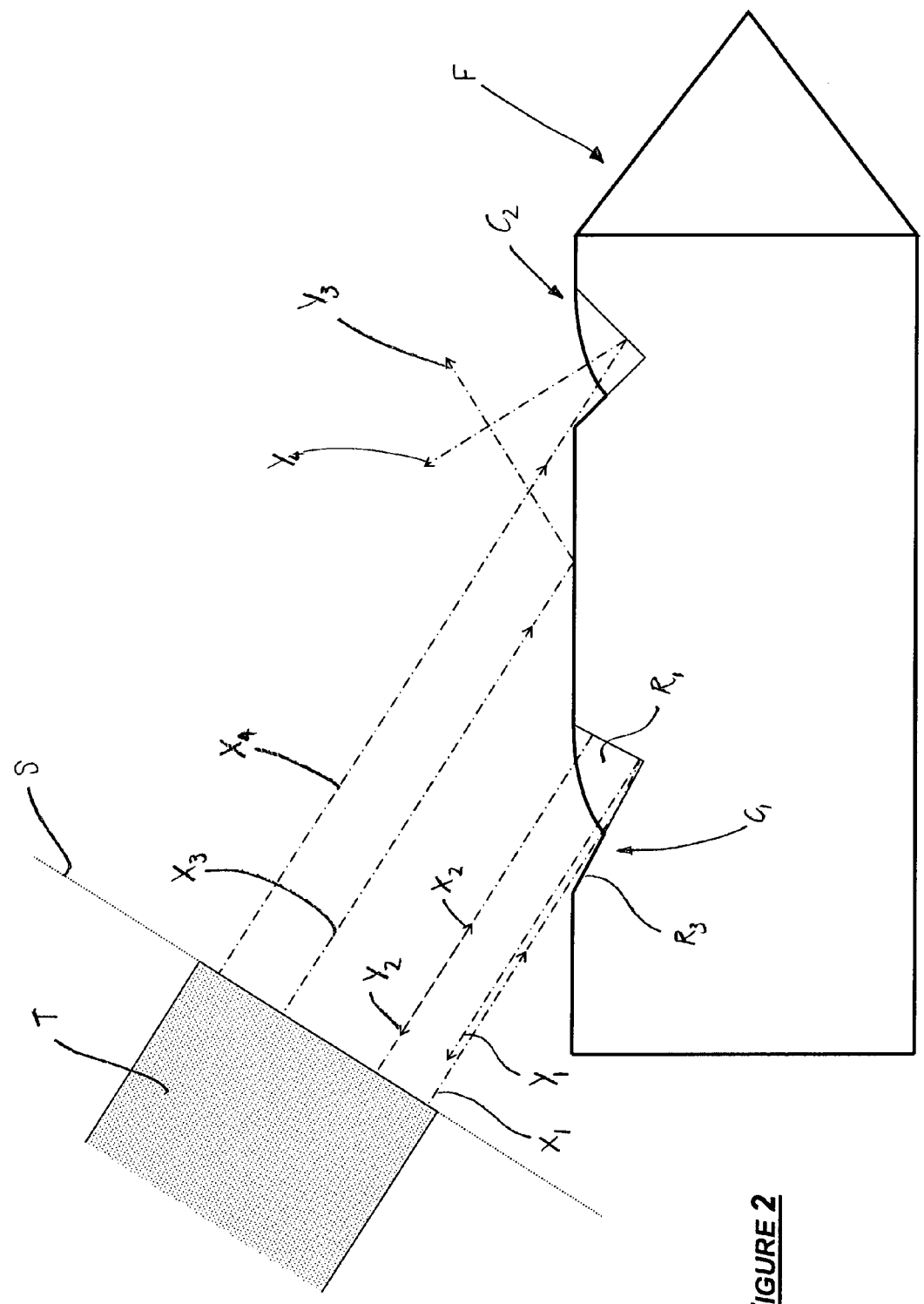
FIG. 2: is a reference schematic cross section view of a needle provided with an ultrasonic reflector according to an embodiment of the invention.

FIG. 2 is a schematic view showing a notional medical needle F in cross section, and a ultrasound transducer T. The needle F has an ultrasonic corner reflector $C_1$ that is orientated in the same configuration as the corner reflector 16 of the needle 10 shown in FIG. 1. The needle F also has a corner reflector $C_2$ with all lines of intersection inclined at 45° to a line extending radially outwardly from the vertex. FIG. 2 is provided merely to more clearly demonstrate the comparative reflections of each of the corner reflectors $C_1$ and $C_2$.

The transducer T includes an emitter for emitting ultrasonic energy, and a receiver for receiving ultrasonic energy. For optimal performance, the proceduralist places the transducer T directly against a patient's outer skin layer S. Ultrasound waves $X_1$, $X_2$, $X_3$, $X_4$ that have been emitted by the transducer T propagate through patient's tissue (not shown) towards the needle F. The emitted ultrasound waves are parallel and, in this particular instance approach the needle F at an angle of approximately 30° to the longitudinal axis of the needle F.

The ultrasound wave $X_1$ that impinges on the corner reflector $C_1$ is reflected by all three reflector surfaces $R_1$, $R_2$, with the reflected ultrasound wave $Y_1$ travelling back towards the transducer T. Similarly, the ultrasound wave $X_2$ that impinges on the corner reflector $C_1$ is reflected by reflector surfaces $R_1$, $R_2$, with the reflected ultrasound wave $Y_2$ also travelling back towards the transducer T.

With the needle F in this orientation, all ultrasound waves, including $Y_1$, $Y_2$, that are reflected by corner reflector $C_1$, including $Y_1$, $Y_2$, travel parallel to the emitted waves X, and back towards the transducer T. The transducer receives the waves $Y_1$, $Y_2$ and consequently the ultrasound image shows the location of corner reflector $C_1$.

Ultrasound wave $X_3$ impinges on the bare surface of the needle F (that is, neither corner reflector $C_1$ nor $C_2$), which is at an oblique angle to wave $X_3$. The reflected ultrasound wave $Y_3$ travels away from the transducer T.

For ultrasound waves X angles between the longitudinal axis of the shaft and transducer of less than 45°, the reflector surface of the corner reflector $C_2$ that is rearward of the vertex becomes "hidden" from the ultrasound waves emitted from the transducer T. Consequently, ultrasound waves that impinge on the corner reflector $C_2$, including wave $X_4$, can only be reflected by only two of the three reflector surfaces. As shown in FIG. 2, once the rearward reflector surface becomes "hidden", the corner reflector $C_2$ tends to reflect ultrasound waves away from the transducer T. In particular, the ultrasound waves (such as reflected wave $Y_3$) that is reflected by corner reflector $C_2$ travels away from the transducer T. Consequently, the corner reflector $C_2$ produces, at best, a weak reflection that may be visible in the ultrasound image.

As will be appreciated, in embodiments of the present invention the orientation of the reflector may be optimized to the relative angles of the needle and emitted ultrasound waves that commonly occur during medical procedures.

Needles according to embodiments of the present invention may also enable the reflector to be visible in an ultrasound image over a range of axial rotational positions of the needle during a procedure. In embodiments in which the reflector is a corner reflector, and where the relative orientation of the needle and the emitted ultrasound waves is such that emitted waves are parallel to the rearmost surface of the reflector or at an angle to impinge on that rearmost surface, the range of axial rotational positions in which the corner reflector's vertex is clearly visible is approximately +/−60° (where 0° corresponds with the plane of the ultrasound waves emitted by the transducer that includes the line extending radially outwardly from the vertex). This large range of axial rotational positions is also because the orientation of the corner reflector on the needle is optimized to the relative angular positions of the needle and emitted ultrasound waves that are likely to occur during medical procedures.

Figure 3:
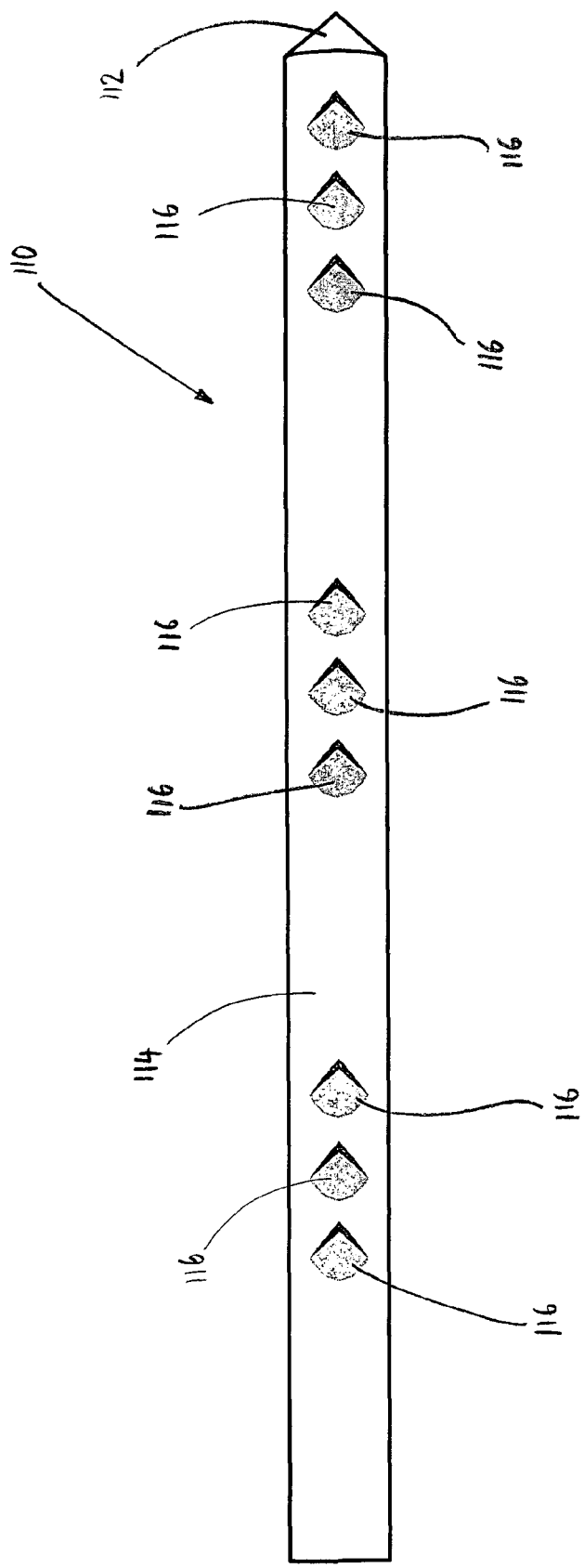
FIG. 3: is a side elevation view of a medical needle according to a second embodiment of the present invention.

FIG. 3 shows a medical needle 110 according to a second embodiment of the present invention. Features of the needle 110 that are correspond with features of the needle 10 are indicated with corresponding reference numerals that have the prefix '1'.

The medical needle 110 has a number of ultrasonic corner reflectors 116 that are arranged in a series linearly along the outer surface of the needle 110 with respect to the axial direction of the needle 110. All corner reflectors 116 within the series are identical in orientation and configuration. The series is configured to provide the proceduralist with a recognizable scale along the needle, making it easier to appreciate distances when moving the needle inside tissue. This can be useful in guiding the needle tip 112 around and/or within features of the surrounding tissue.

For example, the tip 112 may need to be placed immediately adjacent a nerve. The series of corner reflectors 116 allows the proceduralist to estimate the distance of the tip 112 from the nerve, and thus how much further the needle 110 needs to be inserted in order to place the tip 112 in the desired position.

In this embodiment, the series has a repeating pattern of: three corner reflectors 116 that are spaced over a nominal unit length, and a smooth (or "bare") section of needle shaft, which is also of the nominal unit length. Furthermore, the distance between the tip 112 and the start of the series can be selected to suit the needle 110 and/or the intended procedures in which the needle 110 is to be used. The nominal unit length can also be selected to suit the intended procedures in which the needle 110 is to be used, and in particular the required accuracy of placement of the needle tip 112. The nominal length could be, for example, 5 millimetres. This nominal length may be advantageous in an ultrasound imaging system that provides image magnification information by a scale in 10 millimetre (that is, 1 centimetre) increments.

It will be appreciated that the series may be configured with other patterns. Furthermore, other the nominal unit lengths can be employed.

The needle 110 has a single series of corner reflectors 116. In some alternative embodiments, the needle can have two or more series of corner reflectors, in which each series extends longitudinally along the outer surface of the shaft. In this way, the needle can be visible on an ultrasound image in a greater range of axial rotational positions, relative to the ultrasound transducer.

Figure 4:
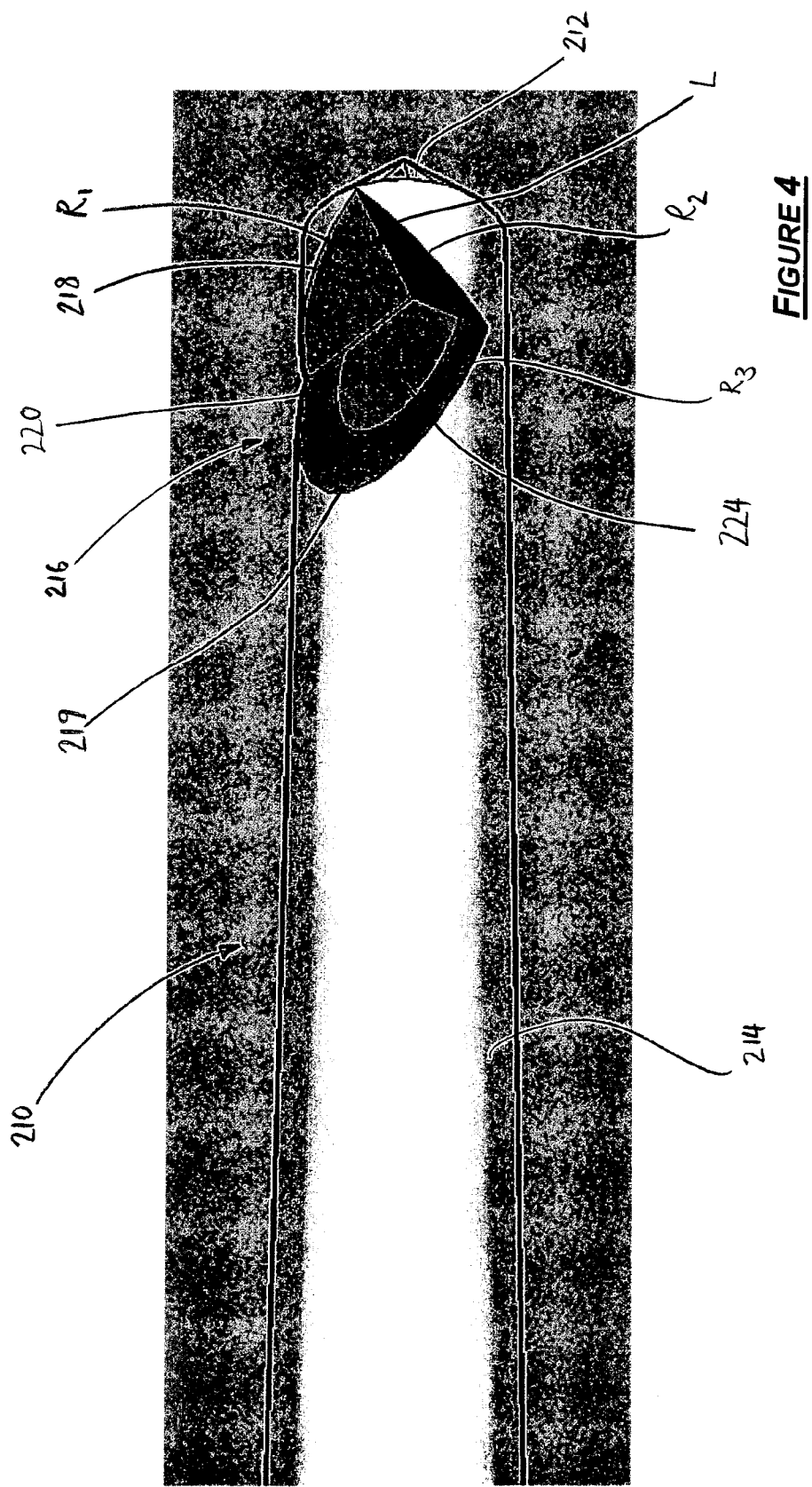
FIG. 4: is a perspective view of a medical needle according to a third embodiment of the present invention.

FIGS. 4 to 6 show a medical needle 210 according to a third embodiment of the present invention. Features of the needle 210 that are correspond with features of the needle 10 are indicated with corresponding reference numerals that have the prefix '2'.

The needle 210 has a lateral injection port 220 positioned rearwardly from the needle tip 212. An ultrasonic reflector 216 is formed in the shaft 214. In this embodiment, the reflector 216 is in the form of a corner reflector. As shown in FIG. 6, the depth of the vertex 218 (from the side wall of the shaft 214) is deeper than the thickness of the tubular wall of the needle 210. In this way, the corner reflector 216 is formed in the port 220.

The needle 210 also has a removable stylet 222 that extends through the lumen of the needle 210 and, when fully inserted, closes off the port 220. The stylet 222 improves the quality of the ultrasound waves reflected by the corner reflector 216. To this end, the forward end of the stylet 222 includes an oblique planar surface 224 that forms the third reflector surface $R_3$ of the corner reflector 216, together with the wall surface 219 of the needle shaft 214.

FIG. 6 illustrates the orientation of the corner reflector 216. The corner reflector 216 has a line of intersection L formed between two surfaces $R_1$, $R_2$. This line extends from the corner reflector vertex 218 towards the needle tip 212. The line of intersection L forms an angle α of 25° with a line P extending radially outwardly of the needle 210 from the corner reflector vertex 218. (It may be noted that in FIG. 5, the line P would extend directly out of the page.)

The third surface $R_3$ of the corner reflector 216 is inclined rearwardly from the vertex 218 and away from the needle tip 12. In this embodiment, the angle of inclination β relative to the line P is 65°. In other words, in this embodiment the third surface $R_3$ is at an angle of 25° to the longitudinal axis of the needle 210, and faces towards the tip 212.

Of course, the oblique planar surface 224 of the stylet 222 is to be inclined at the same angle as the wall surface 219. Accordingly, the oblique planar surface is at an angle of 25° to the longitudinal axis of the needle 210.

The needle 210 and stylet 222 can each have markers (not shown) to allow the proceduralist to confirm that alignment of the planar surface 224 within the lumen of needle 210. In this way, the planar surface 224 and wall surface 219 can be aligned to form a mutually planar surface for reflecting ultrasound waves.

In certain embodiments, fluid, a catheter and/or a wire can be passed through the lumen of the needle 210 and out through the port 220.

Figure 7:
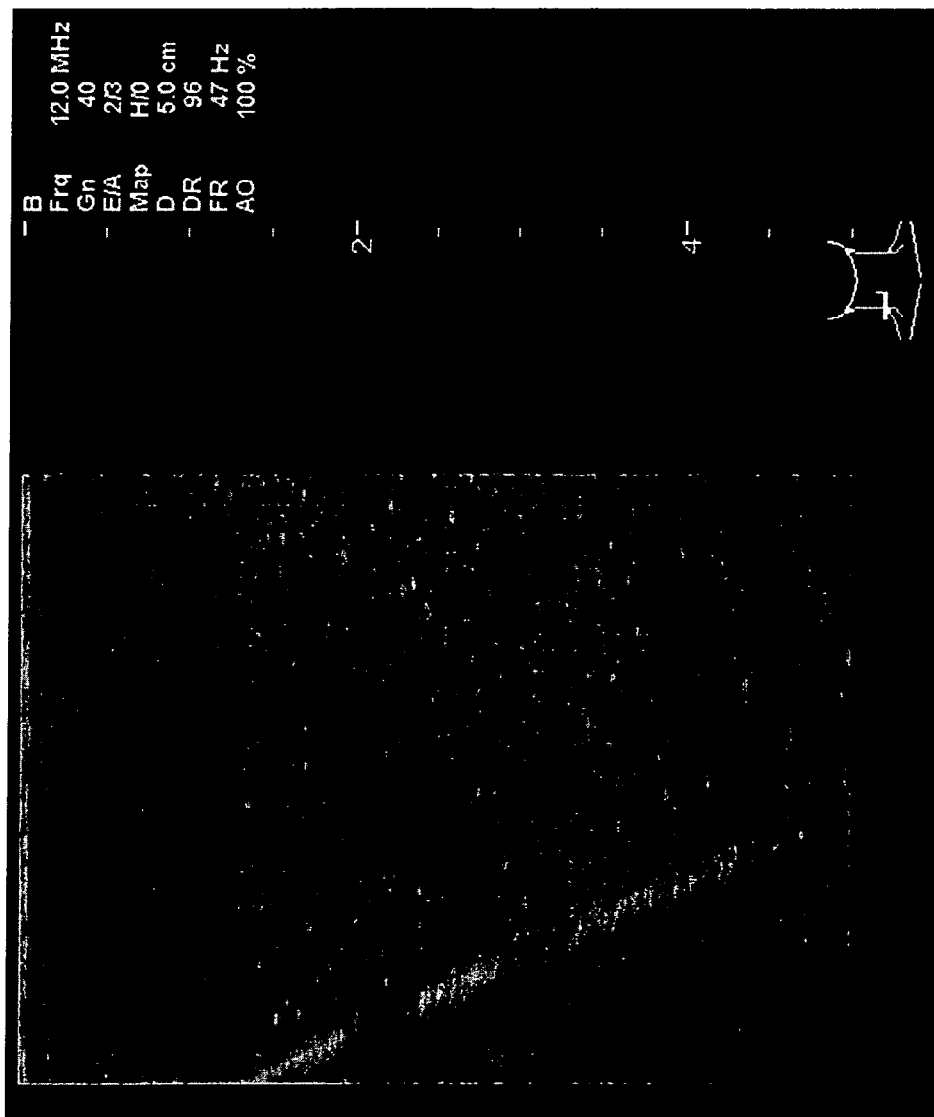
FIG. 7: is an ultrasound image of a needle in pig tissue, the needle being in accordance with a fourth embodiment of the present invention.

FIG. 7 shows an ultrasound image of a medical needle 310 in accordance with a fourth embodiment, which is embedded in pig tissue. The needle 310 has a series of ultrasonic reflectors that are arranged longitudinally along the outer surface of the needle shaft (which is not visible in FIG. 7). In this embodiment, the reflectors are corner reflectors and are orientated on the needle shaft in the same manner as those of the needle 110.

Due to the effects of noise and diffusion of the reflected ultrasound waves, the corner reflectors are slightly blurred in the ultrasound image. In spite of these effects, the corner reflectors are clearly visible. Commencing from the needle tip 312 and extending rearwardly along the shaft, the series has a repeated sequence consisting of: a plurality of corner reflected over 5 mm, a smooth section over 2.5 mm, a plurality of corner reflected over 2.5 mm, and a smooth section over 2.5 mm. Therefore, in this embodiment, the series is constructed with a nominal unit length of 2.5 mm.

In the ultrasound image, the image scale is shown (in centimetres) to the right of the tissue section. The needle 310 is embedded in the tissue at an angle of approximately 65° to the tissue surface. The needle tip 310 is at a depth of 42 mm (4.2 cm).

FIGS. 8 to 15 show a medical needle 410 according to a fifth embodiment of the present invention. Features of the needle 410 that are correspond with features of the needle 10 are indicated with corresponding reference numerals that have the prefix '4'.

The needle 410 has a plurality of ultrasonic reflectors 416 that each have two reflector surfaces $R_1$, $R_2$ that are concave in the direction of a third reflector surface $R_3$. In other words, lines that are normal to the respective reflector surfaces $R_1$, $R_2$ are convergent.

The reflectors 416 that are arranged in six series along the outer surface of the needle 410. All reflectors 416 within each series are identical in orientation and configuration. Furthermore, as shown most clearly in FIG. 15, each reflector 416 is symmetrical about a plane that includes the longitudinal axis of the needle shaft 412. Thus, the angle $\theta$ between the longitudinal axis of the needle and each of the reflectors surfaces $R_1$, $R_2$ is identical.

Figure 12:
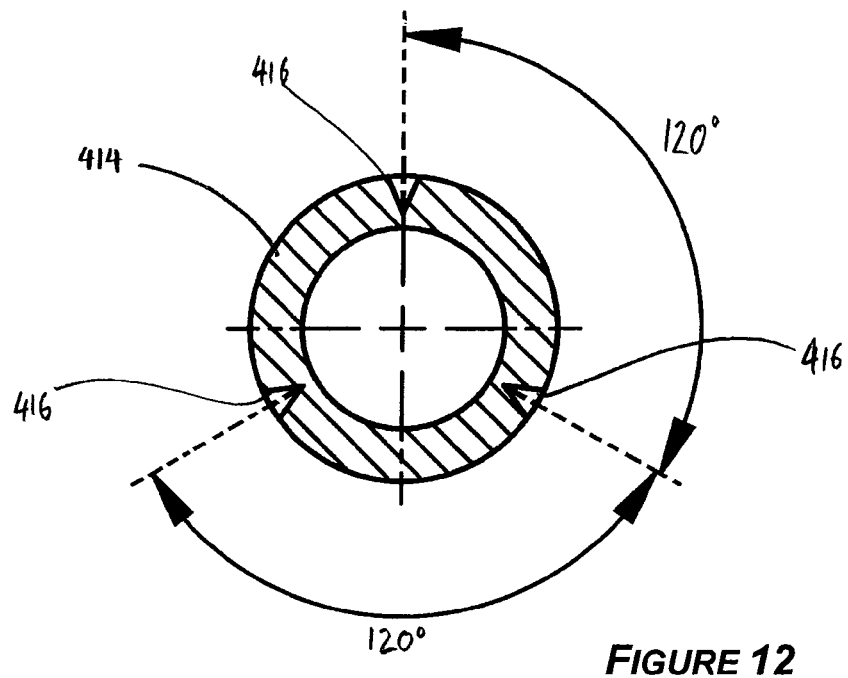
FIG. 12: is a cross section view of the needle of FIG. 8, as viewed along the line A-A in FIG. 11.
Figure 13:
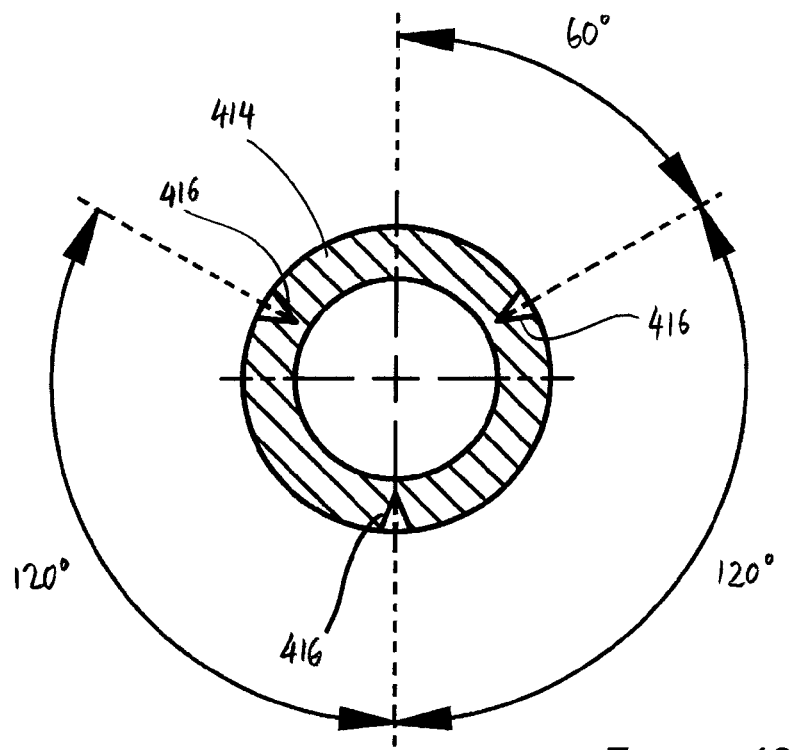
FIG. 13: is a cross section view of the needle of FIG. 8, as viewed along the line B-B in FIG. 11.

As illustrated by FIGS. 12 and 13, the six series of reflectors 416 are equally spaced in a circumferential direction around the outer surface of the needle shaft. Thus, an angular separation of 60° is provided between adjacent series of reflectors 416. Furthermore, each series is offset longitudinally with respect to the adjacent series. Consequently, three of the six series of reflectors 416 are closer to the tip 412 than the other three series.

Figure 8:
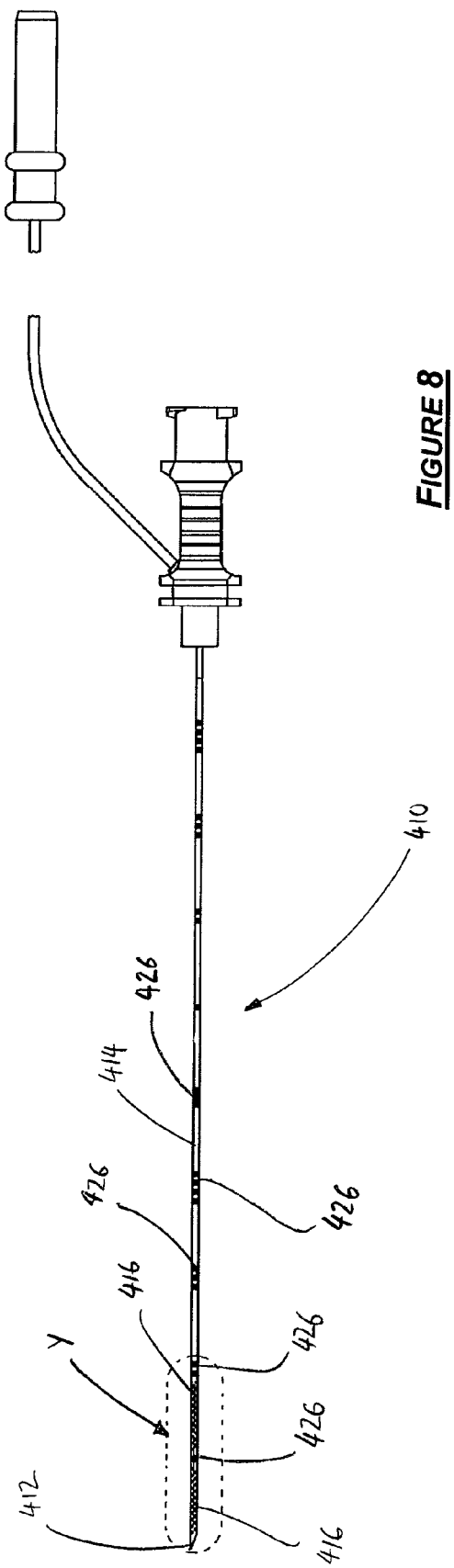
FIG. 8: is a side elevation view of a medical needle according to a fifth embodiment of the present invention.
Figure 11:
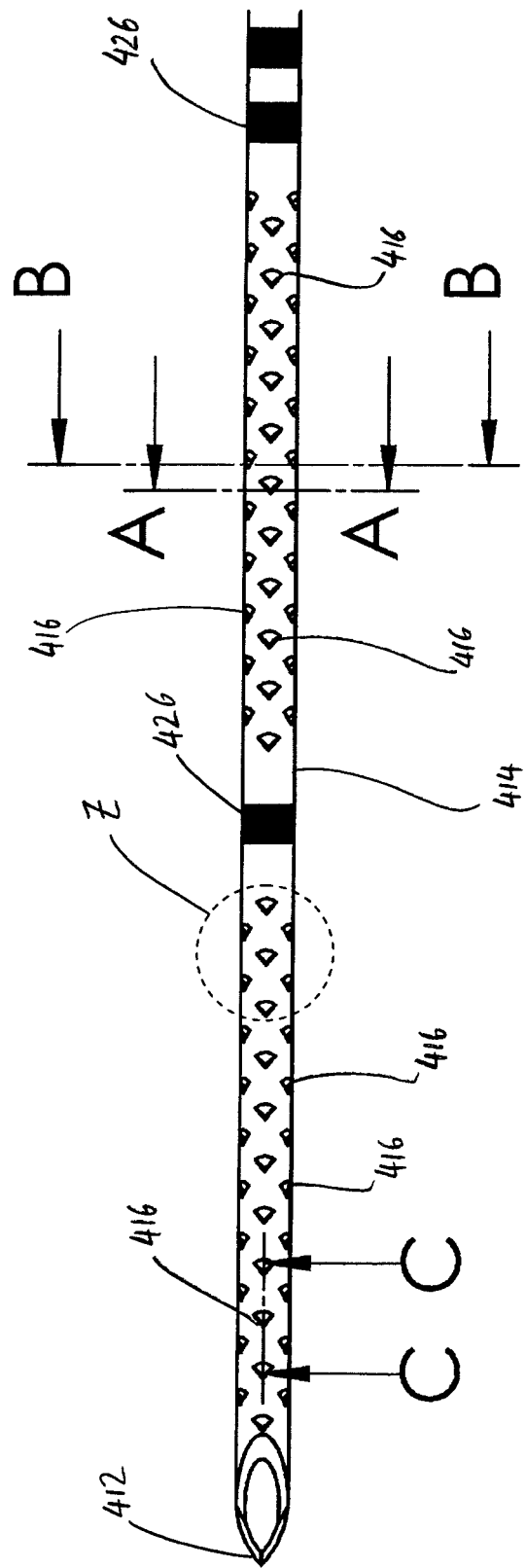
FIG. 11: is a bottom view of region Y of the needle of FIG. 8.

As shown most clearly in FIG. 8, the needle 410 has graduations, which in this embodiment are in the form of contrasting circumferential bands 426. The bands 426 are provided on the outer surface of the needle. The spacing of adjacent graduations is the same, and also the same as the spacing of the foremost graduation from the needle tip 412. The graduations provide the proceduralist with a visual indication of the depth of the needle tip 412 based on the portion of the needle 410 that is external to the patient. Each of the six series of reflectors 416 consists of two sets of reflectors 416 that are spaced longitudinally along the shaft 414 of the needle 410. Thus, there is a region of "bare" needle shaft (that is, needle shaft without reflectors formed in the outer surface) between each set of reflectors 416.

The foremost band 426 is provided on the outer surface between the sets of reflectors 416 in the six series. As can be seen in the ultrasound images shown in FIGS. 23 and 24, the reflectors 416 show up on the ultrasound image as a line of prominent white spots. The separation between sets of reflectors 416 in the series indicates the needle position in a manner that is consistent with the graduations.

In this particular embodiment, the length of each set of reflectors 416 within each series is approximately 9 millimetres, and the separation of the sets is approximately 2 millimetres. In addition, the graduations are provided at 10 millimetre centres.

Figure 14:
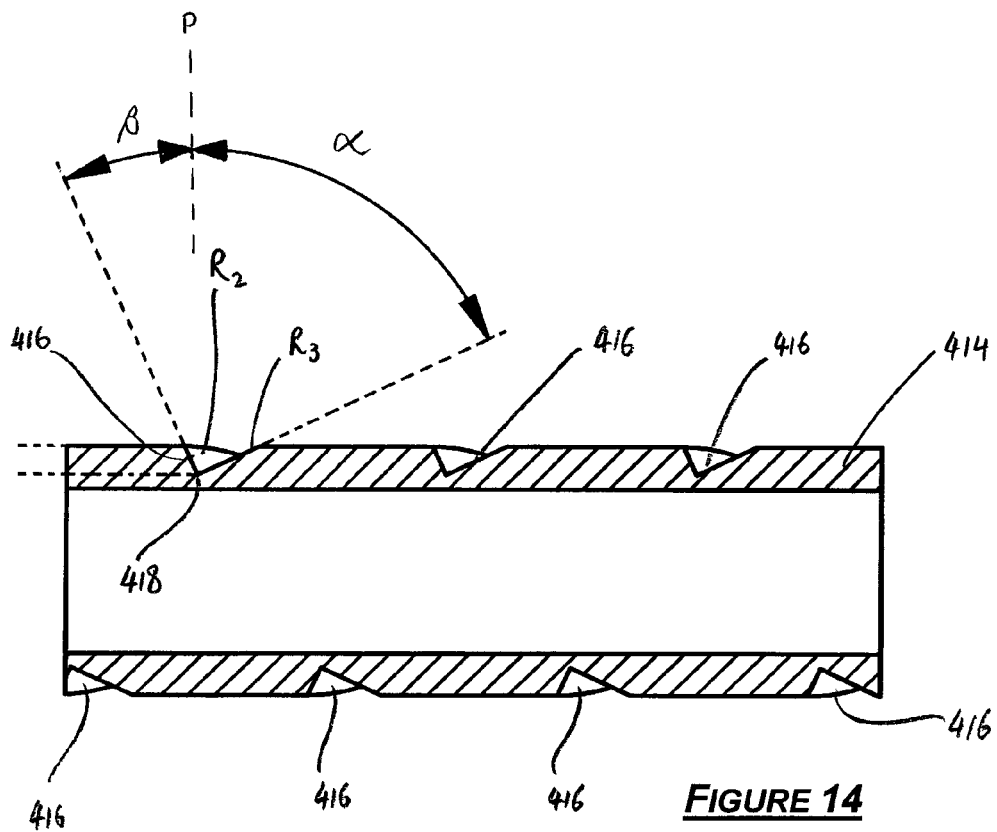
FIG. 14: is a cross section view of the needle of FIG. 8, as viewed along the line C-C in FIG. 11.
Figure 15:
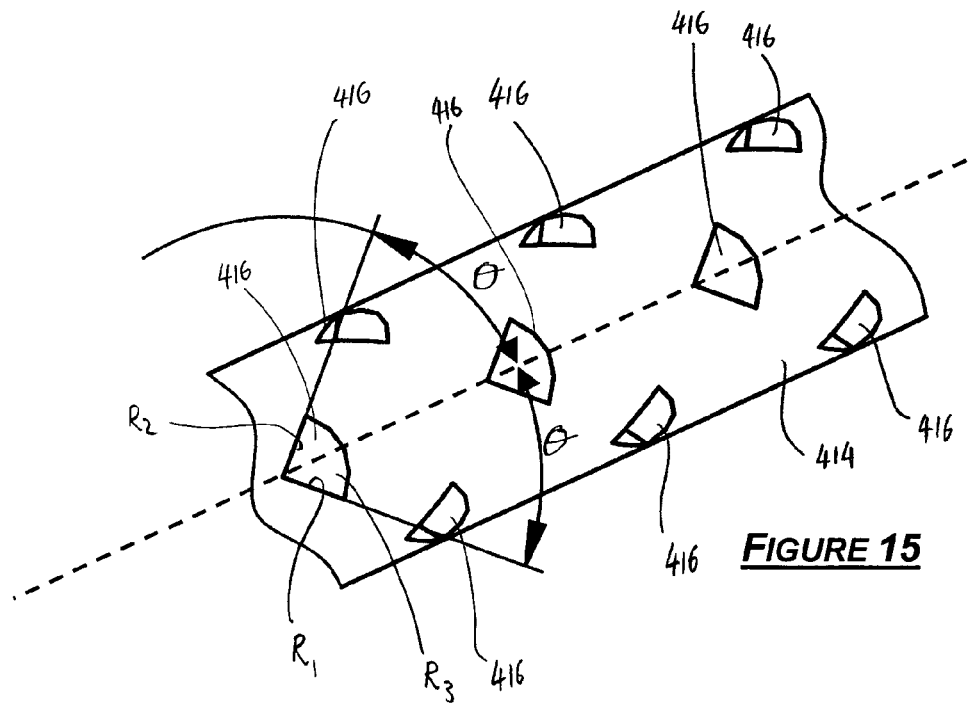
FIG. 15: is a perspective view of region Z of the needle of FIG. 11.

As shown in FIG. 14, the depth of the vertex 418 of the reflector 416 is less than the wall thickness of the needle 410. In FIG. 14, the needle tip is towards the left of the page. It will be appreciated that forming reflectors 416 in the outer surface of the needle 410 results in a decrease in wall thickness, which can compromise the structural integrity of the needle.

In FIG. 14, line P extends radially outwardly of the needle 410 from the reflector vertex, and thus is perpendicular to the longitudinal axis of the needle 410. Angle $\alpha$ corresponds with the acute angle between the first reflector surface $R_3$ and the longitudinal axis. In this embodiment, $\alpha$ is 65°. Angle $\beta$ corresponds with the acute angle between the line of intersection between the additional reflector surfaces $R_1$, $R_2$ and the longitudinal axis. In this embodiment, $\beta$ is 25°.

The arrangement of the series of reflectors 416 described above enables the number of reflectors provided on the shaft 414 of the needle to be maximized, whilst maintaining sufficient structural integrity of the needle 410.

Figure 16:
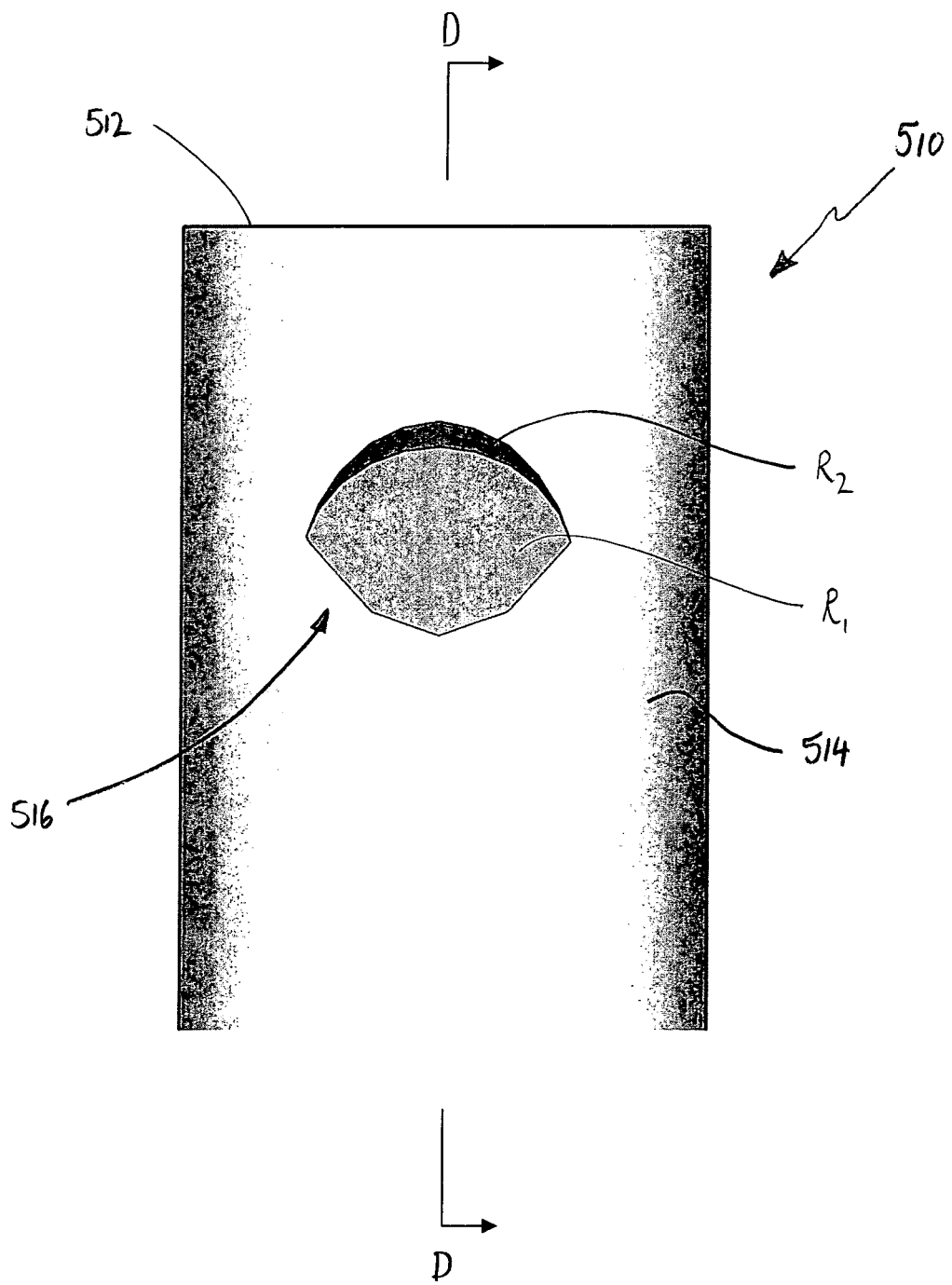
FIG. 16: is a side elevation view of a medical needle according to a sixth embodiment of the present invention.

FIGS. 16 to 18 show a medical needle 510 according to a sixth embodiment of the present invention. The needle 510 has a needle tip 512 at one end of the shaft 514. In this embodiment, the needle 510 defines a lumen 515 through which to deliver fluid, and/or extract tissue, fluid or cells during a procedure. The needle shaft 514 defines a longitudinal axis.

The needle 510 has an ultrasonic reflector 516 formed in the outer surface of the needle shaft 514. The reflector 516 has a first reflector surface $R_1$ that is at an angle of no more than 35° to the longitudinal axis, and that faces towards the tip 512. In this embodiment, the first reflector surface $R_1$ is at an angle of approximately 20° to the longitudinal axis. The reflector 516 also has an additional reflector surface $R_2$ that is curved and is concave in the direction of the first reflector surface $R_1$. Due to the curved shape of the additional reflector surface $R_2$, lines that are normal to the reflector surface $R_2$ are convergent.

In this embodiment, the reflector surface $R_2$ is in the form of a circular arc. Accordingly, in this embodiment all lines that are normal to the reflector surface $R_2$ converge on the centre of radius of the reflector surface $R_2$.

The reflector surface $R_2$ subtends an angle of 90°. However, in alternative embodiments, the additional reflector surface can subtend an angle in the range of 60° to 180°.

Ultrasound waves that impinge on the reflector 416 are reflected by at least the reflector surface $R_2$, and in many instances both reflector surfaces $R_1$, $R_2$. Where an incident ultrasound wave travels in a direction that is in the plane that also includes a line normal to the reflector surface $R_2$, a portion of the wave may be reflected back towards the transducer in a direction parallel to the incident wave.

Figure 19:
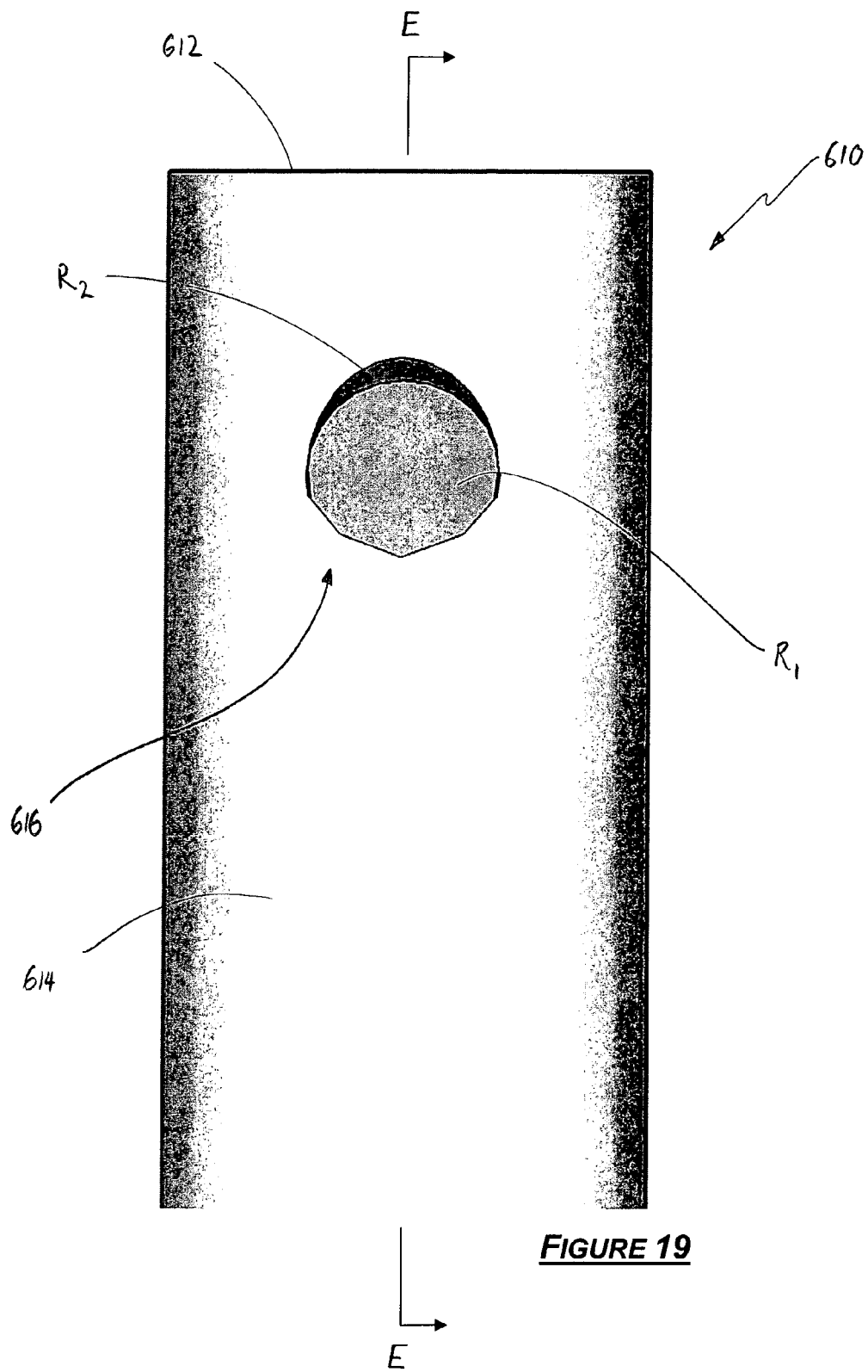
FIG. 19: is a side elevation view of a medical needle according to a seventh embodiment of the present invention.
Figures 20, 21:
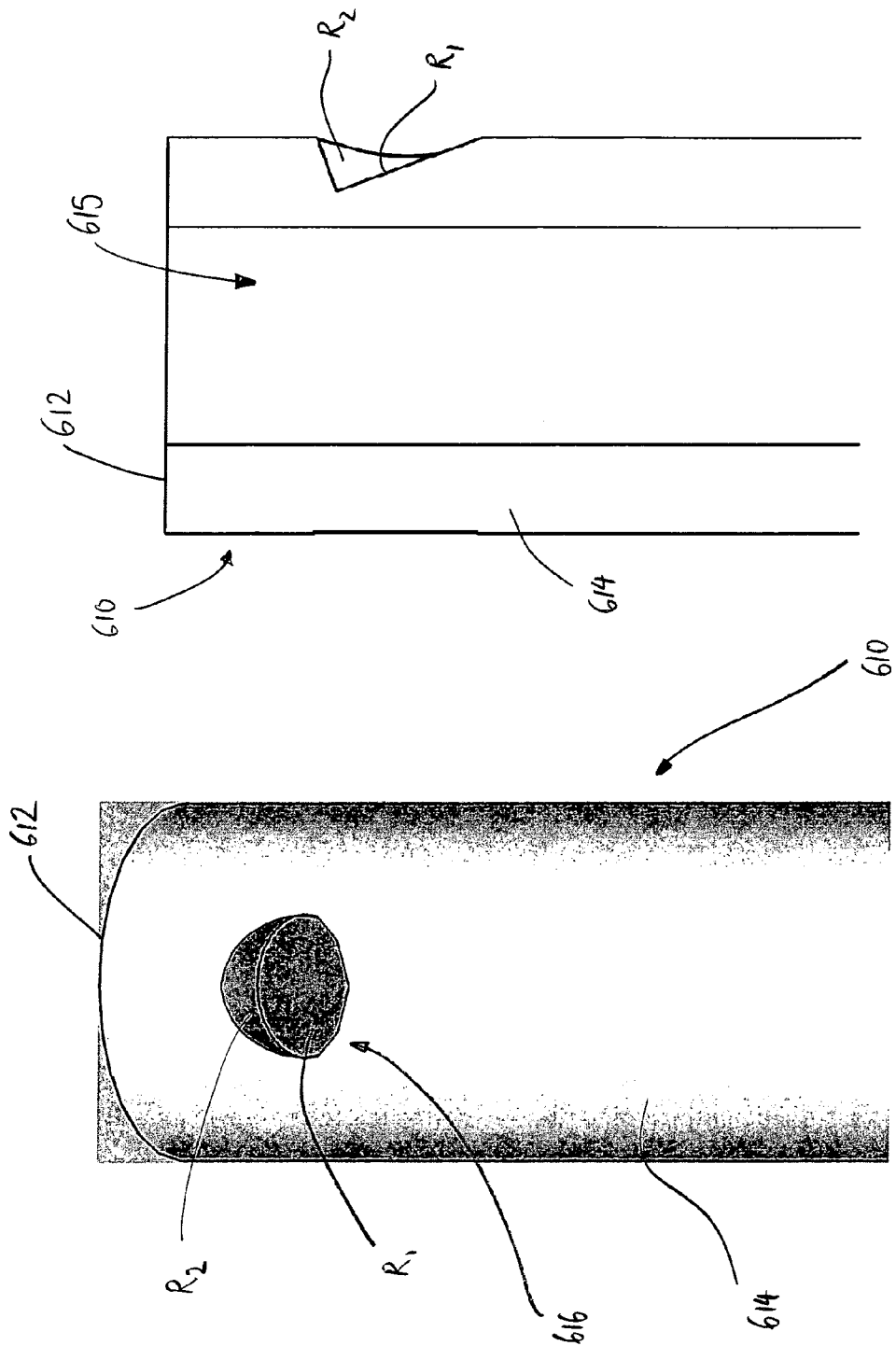
FIG. 20: is a rear perspective view of the needle of FIG. 19.
FIG. 21: is a cross sectional view of the needle of FIG. 19, as viewed along the line E-E.

FIGS. 19 to 21 show a medical needle 610 according to a seventh embodiment of the present invention. The needle 610 has a needle tip 612 at one end of the shaft 614. The needle 610 defines a lumen 615 through which to deliver fluid, and/or extract tissue, fluid or cells during a procedure. The needle shaft 614 also defines a longitudinal axis.

The needle 610 has an ultrasonic reflector 616 formed in the outer surface of the needle shaft 614. The reflector 616 has a first reflector surface $R_1$ that is at an angle of no more than 35° to the longitudinal axis, and that faces towards the tip 612. In this embodiment, the first reflector surface $R_1$ is at an angle of approximately 20° to the longitudinal axis. The reflector 616 also has an additional reflector surface $R_2$ that is curved and is concave in the direction of the first reflector surface $R_1$.

The reflector 616 differs from the reflector 516 in that the reflector surface $R_2$ subtends an angle of 135°.

In embodiments of FIGS. 16 to 19, the ultrasonic reflector has a first reflector surface that is inclined to the longitudinal axis of the needle and faces towards the needle tip and a curved reflector surface that is inclined to the first reflector surface. There is a curved line of intersection between the two reflector surfaces. In such embodiments, where the relative orientation of the needle and the emitted ultrasound waves is such that emitted waves are parallel to the first reflector surface or at an angle to impinge on that surface, the range of axial rotational positions in which the line of intersection is clearly visible is approximately +/−60° (where 0° corresponds with the plane of the ultrasound waves emitted by the transducer that is co-incident with a plane of symmetry of the reflector).

In the embodiments illustrated in FIGS. 16 to 19, the needles have been illustrated with a straight-cut tip. It will be appreciated that the needle tip shape is not significant to the present invention.

Figure 22:
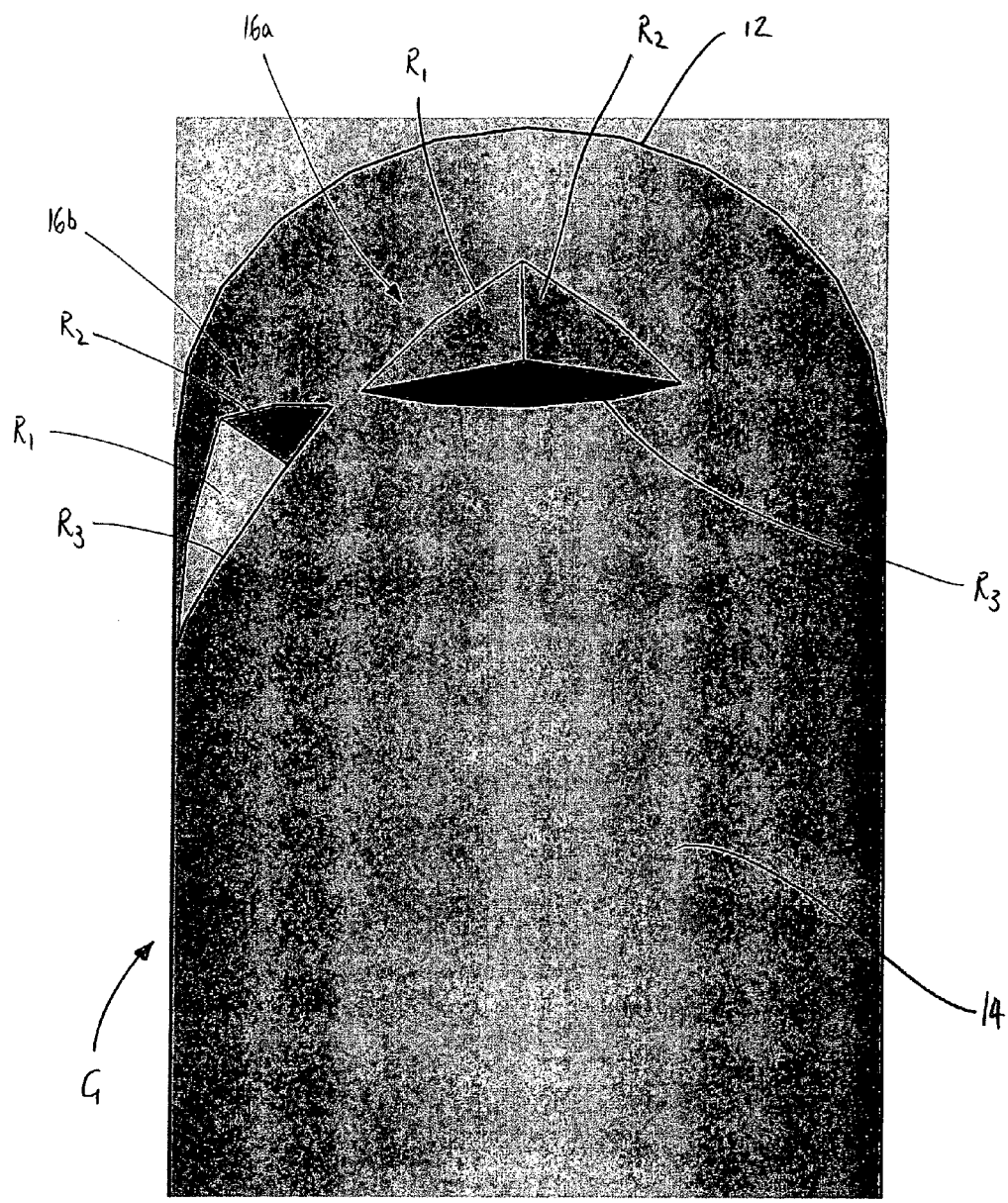
FIG. 22: is a reference perspective view of a needle with two reflectors in accordance with the present invention.

FIG. 22 is a reference perspective view showing a notional needle G that includes two ultrasonic reflectors 16a, 16b of the type described previously in connection with FIGS. 1 to 15. The two reflectors 16a, 16b are circumferentially spaced in the outer surface of the needle shaft 14, with an angular separation of 60° therebetween. The reflectors 16a, 16b are also positioned at the same distance from the tip 12 of the needle G. The needle G is inclined with the longitudinal axis at an angle of approximately 30° to the plane that includes the page. This inclination corresponds with a steep angle of insertion.

In FIG. 22, the needle G is orientated such that ultrasonic reflector 16a is centred in the illustrated view. All three reflector surfaces $R_1$, $R_2$, $R_3$ of reflector 16a are visible.

Due to the circumferential spacing between the two reflectors 16a, 16b, reflector 16b is rotated 60° counter-clockwise in the illustrated view. The additional reflector surfaces (that is, reflector surfaces $R_1$, $R_2$) of reflector 16b are visible in FIG. 22. However, due to the inclination of the needle G in this view, the first reflector surface $R_3$ lies in a plane that is perpendicular to the page. Accordingly, the vertex of reflector 16b also lies in this plane.

If ultrasound waves are transmitted in a plane that is perpendicular to the page and includes the longitudinal axis of the needle G, both reflectors 16a, 16b are able to reflect impinging ultrasound waves back to the source in a direction parallel to the incident ultrasound waves.

FIG. 22 demonstrates that reflectors according to some embodiments of the present invention are visible through a range of angles from −60° to +60°, where 0° corresponds with the line extending radially outwardly from the vertex and lying in the plane of the ultrasound waves emitted by the transducer.

In the embodiment described with reference to FIGS. 8 to 15, a proceduralist is able to insert a needle 410 in the patient and rotate the needle 410 without loss of echogenicity.

It will be appreciated that with sufficient rotation of the needle 416 about its longitudinal axis, the vertex of the reflector 410 becomes shadowed by the needle shaft 414. Similarly, as the angle between the incident ultrasound waves and the longitudinal axis of the needle 410 approach parallel, the vertex of the reflector 410 also becomes shadowed by the needle shaft 414. Reflectors according to embodiments of the present invention maximize the echogenicity of the reflector for a broad range of rotational angles about the longitudinal axis, and also for a broad range of angles that, in practice, are encountered during ultrasound guided procedures.

FIGS. 23 and 24 show an ultrasound image of the needle 410 embedded in gelatin. FIG. 23 shows the needle 410 at a moderate angle of insertion of approximately 55° to the ultrasound transducer. FIG. 23 shows the needle 410 at a steep angle of insertion of approximately 25° to the ultrasound transducer. In both images, the reflectors 416 are clearly shown as two lines of prominent white spots, with the dark region between the lines indicating the region of bare needle between the sets in each of the six series. Clearly, in FIGS. 23 and 24, the needle tip 412 is immediately adjacent the lowest reflector 416, which facilitates rapid identification of the location of the needle tip 412.

In needles according to embodiments of the invention, the visibility of a reflector in the ultrasound image is influenced by its orientation on the needle shaft, among other factors. In particular, decreasing the angle between the first reflector surface and the longitudinal axis can improve the visibility of the reflector at steep angles of insertion. However, the wall thickness of a needle is limited by lumen size, and the requirement that the needle be sufficiently rigid. For this reason, the maximum depth of the reflector is also limited. Therefore, as the angle ($\alpha$) between the first reflector surface and the longitudinal axis decreases, the area of each of the surfaces $R_1$, $R_2$ on either side of the line of intersection L also decreases. Accordingly, the visibility of the corner reflector can decrease with a decrease in the angle ($\alpha$). There is an optimal range of angles ($\alpha$) between the first reflector surface and the longitudinal axis of the needle. It is envisaged that this range is: $10° \leq \alpha \leq 35°$.

The needles of the embodiments described in connection with FIGS. 1, and 3 to 6 are pencil point needles. The needle of the embodiment described in connection with FIGS. 8 to 15 is a bevel tipped needle. However, it is to be appreciated that any needle leading edge/tip shape can be employed.

In the embodiments described in connection with FIGS. 1, 3, 7 to 21, 23 and 24, the maximum depth of the reflector(s) from the maximum radius of the needle shaft is less than the maximum wall thickness of the needle shaft.

Invasive medical procedures using needles according to embodiments of the present invention can involve:
providing an ultrasonic transducer;
placing the transducer on a patient's outer skin and energizing the transducer to emit ultrasound waves into the patient;
inserting the needle into the patient adjacent the transducer such the ultrasound waves impinge on a portion of the needle that includes the ultrasonic reflector; and
capturing a reflected ultrasonic wave from the ultrasonic reflector.

The reflected ultrasonic wave from the reflector that is captured by the transducer can then be used to generate an ultrasound image.

Since many ultrasound transducers emit a plane of ultrasound waves, it can be beneficial to insert the needle with its longitudinal axis lying in the plane that includes the emitted ultrasound waves.

The proceduralist can establish the angle of insertion of the needle such that the longitudinal axis of the needle and the emitted ultrasound waves form an angle that is at least equal to the angle of the first reflector surface relative to the longitudinal axis of the needle. This can involve using the transducer to identify the region in which the needle tip should be deployed for the necessary procedure, and then inserting the needle into the patient. Alternatively or additionally, this may involve inserting the needle into the patient, and then locating the needle and also the region in which the tip is to be deployed with the transducer.

For the purposes of this specification, the term "needle" is intended to include conventional needles, and medical devices that have needle-like structure, including, but not limited to, catheters, guide wires, cannulae, access ports and trocars. Embodiments of the present invention can be employed in any tissue piercing procedure, regardless of whether the needle is used to transport material through a lumen. For example, embodiments of the present invention may be used in procedures utilizing the Seldinger or railroad techniques, in which the needle simply acts as a guide for a guide wire or catheter.

Procedures in which needles according embodiments of the present invention can be used include (but are not limited to):

a. Intravascular cannulation, in which the present invention enables guidance into vessels that can not be felt, such as large central veins and small peripheral veins;
 b. Peripheral nerve block, particularly in anaesthesia, to place local anaesthetic near the nerve to send it asleep for either surgery or pain relief;
 c. Biopsy of tissues:
   i. Cell aspiration; and
   ii. Core biopsy;
 d. Amniocentesis and choriovillous sampling;
 e. Brachytherapy;
 f. Botox treatment of deep muscle;
 g. Drainage of fluid, such as pericardial, pleural, or abdominal;
 h. Percutaneous Nephrostomy;
 i. Suprapubic catheters;
 j. Laparoscopic surgery and/or diagnostics.

In all the above mentioned procedures (and others), the needle is commonly inserted into the patient at a large angle to the skin, and at a small angle to the ultrasound transducer.

In certain embodiments of the present invention, needles can combine other needle location technologies. For example, needles of the present invention can be provided with insulation to enable the proceduralist to utilize electro-nerve stimulation techniques.

It will be appreciated that in some embodiments, the additional reflector surfaces may include three or more reflector surfaces.

It will be appreciated that procedures employing embodiments of the present invention can be performed on both human and animal patients.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A medical needle comprising a needle shaft that defines a longitudinal axis, a tip formed at one end of the needle shaft, and an ultrasonic reflector formed in an outer surface of the needle shaft, the reflector comprising:
   a first reflector surface that is formed in the outer surface of the needle shaft at an angle of no more than 35° to the longitudinal axis of the needle shaft and that faces towards the tip of the needle, and
   at least one additional reflector surface formed in the outer surface of the needle shaft that forms an angle to the first reflector surface within the range of 75° to 105°, and that is substantially concave in a direction towards the first reflector surface,
   whereby ultrasound waves emitted by an ultrasound transducer can be reflected by the reflector back to the transducer as the needle is rotated about the longitudinal axis of the needle through a range of angles, and wherein the range of angles is approximately −60° to +60°, where 0° corresponds with a rotational position in which a plane of ultrasound waves emitted by the transducer is co-incident with a plane of symmetry of the reflector.

2. A medical needle comprising a needle shaft defining a longitudinal axis, a tip formed at one end of the needle shaft, and an ultrasonic reflector formed in an outer surface of the needle shaft, the reflector comprising:
   a first reflector surface that is formed in the outer surface of the needle shaft at an angle of no more than 35° to the longitudinal axis of the needle shaft and that faces towards the tip of the needle, and
   at least one additional reflector surface formed in the outer surface of the needle shaft that forms an angle to the first reflector surface within the range of 75° to 105°, and that has two or more convergent normals,
   whereby ultrasound waves emitted by an ultrasound transducer can be reflected by the reflector back to the transducer as the needle is rotated about the longitudinal axis of the needle through a range of angles, and wherein the range of angles is approximately −60° to +60°, where 0° corresponds with a rotational position in which a plane of ultrasound waves emitted by the transducer is co-incident with a plane of symmetry of the reflector.

3. A medical needle according to either claim 1 or 2, wherein the reflector is symmetrical about a plane that includes the longitudinal axis of the needle shaft.

4. A medical needle according to either claim 1 or 2, wherein the first reflector surface is at an angle of approximately 20° to the longitudinal axis.

5. A medical needle according to either claim 1 or 2, wherein the first reflector surface is planar.

6. A medical needle according to either claim 1 or 2, wherein the at least one additional reflector surface comprises at least two reflector surfaces that intersect with each other.

7. A medical needle according to claim 6, wherein the at least two additional reflector surfaces are planar.

8. A medical needle according to claim 6, wherein the at least one additional reflector surface consists of two additional reflector surfaces, and wherein the first reflector surface and the two additional reflector surfaces are disposed at an angle to one another within the range of 75° to 105°.

9. A medical needle according to claim 8, wherein the first reflector surface and the two additional reflector surfaces are mutually orthogonal to one another.

10. A medical needle comprising:
   a tip formed at one end of a needle shaft, the needle shaft defining a longitudinal axis, and
   an ultrasonic reflector formed in an outer surface of the needle shaft and having three reflector surfaces that intersect to form a reflector vertex, the reflector being orientated with a first of the three reflector surfaces located entirely rearwardly of the reflector vertex with respect to the needle tip and being at an angle of no more than 35° to the longitudinal axis and facing towards the needle tip, and the reflector being symmetrical about a plane that is co-incident with the longitudinal axis of the needle shaft,
   whereby ultrasound waves emitted by an ultrasound transducer can be reflected by the reflector back to the transducer as the needle is rotated about the longitudinal axis of the needle through a range of angles, and wherein the range of angles is approximately −60° to +60°, where 0° corresponds with a rotational position in which a plane of ultrasound waves emitted by the transducer is coincident with a plane of symmetry of the reflector.

11. A medical needle according to claim 10, wherein the first reflector surface is at an angle to the longitudinal axis within the range of 10° to 35°.

12. A medical needle according to either claim 10 or 11, wherein the first reflector surface is at an angle of 25° to the longitudinal axis.

13. A medical needle according to any one of claim 1, 2, or 10, wherein the reflector is one of a plurality of like reflectors formed in the outer surface of the needle shaft, the plurality of reflectors being arranged in one or more series of reflectors, each series extending linearly along the needle shaft.

14. A medical needle according to claim 13, wherein the or each series consists of two or more sets of reflectors, the sets being spaced longitudinally along the shaft of the needle.

15. A medical needle according to claim 14, further comprising graduations marked on the outer surface of the needle, wherein one of the graduations is disposed between adjacent sets of reflectors in the or each series.

\* \* \* \* \*